(12) United States Patent
Buchold et al.

(10) Patent No.: US 7,589,227 B2
(45) Date of Patent: Sep. 15, 2009

(54) METHOD FOR THE PRODUCTION OF ORGANIC CARBONATES

(75) Inventors: Henning Buchold, Hanau (DE); Jürgen Eberhardt, Rodgau (DE); Ulrich Wagner, Biendorf (DE); Hans-Jörg Wölk, Rosenheim (DE)

(73) Assignee: Lurgi GmbH, Frankfurt am Main (DE)

( * ) Notice: Subject to any disclaimer, the term of this patent is extended or adjusted under 35 U.S.C. 154(b) by 496 days.

(21) Appl. No.: 10/571,476

(22) PCT Filed: Jul. 16, 2004

(86) PCT No.: PCT/EP2004/007911

§ 371 (c)(1),
(2), (4) Date: Oct. 31, 2006

(87) PCT Pub. No.: WO2005/028414

PCT Pub. Date: Mar. 31, 2005

(65) Prior Publication Data

US 2007/0082985 A1     Apr. 12, 2007

(30) Foreign Application Priority Data

Sep. 11, 2003   (DE) ................................ 103 41 953

(51) Int. Cl.
*C07C 69/96* (2006.01)
(52) U.S. Cl. ..................................... 558/260
(58) Field of Classification Search .................. None
See application file for complete search history.

(56) References Cited

U.S. PATENT DOCUMENTS

| | | | |
|---|---|---|---|
| 4,436,668 A | 3/1984 | Harder et al. | 558/260 |
| 5,489,702 A | 2/1996 | Doya et al. | 558/277 |
| 6,031,122 A | 2/2000 | Mizukami et al. | 558/277 |

FOREIGN PATENT DOCUMENTS

| | | |
|---|---|---|
| EP | 0041622 | 12/1981 |
| EP | 0478073 | 4/1992 |
| EP | 0638541 | 2/1995 |
| EP | 0866051 | 9/1998 |

*Primary Examiner*—Kamal A Saeed
(74) *Attorney, Agent, or Firm*—Roberts & Roberts, LLP

(57) ABSTRACT

The invention relates to a method for the production of monomer organic carbonates, wherein urea, substituted urea, a salt or an ester of carbamide acid or one of the N-substituted derivatives thereof is reacted in a first step in a polyalkylene glycol, a polyester-polyol or a polyether-polyol of general formula (I), wherein R represents a linear or branched alkylene group having 2-12 carbon atoms and n is a number between (2) and (20), or in a completely or partially hydrolysed polyvinyl alcohol of general formula (II) wherein R' represents an alkyl group, an aryl group or an acyl group having 1-12 carbon atoms, p and q are numbers between 1 and 20, or in mixtures of said compounds in the presence of a catalyst facilitating the separation of ammonia in order to form a mixture containing carbonates and carbamates, the ammonia becomes free or the amine is removed form the reaction mixture by means of a strip gas. In a second reaction step (transesterification), the mixture containing the carbonates and carbamates is reacted with a monomer alcohol or a phenol whereby monomer carbonates are formed and polymer polyalcohols of formulae (I) or (II) are reformed.

$$H-[O-R]_n-OH \qquad (I)$$

16 Claims, 1 Drawing Sheet

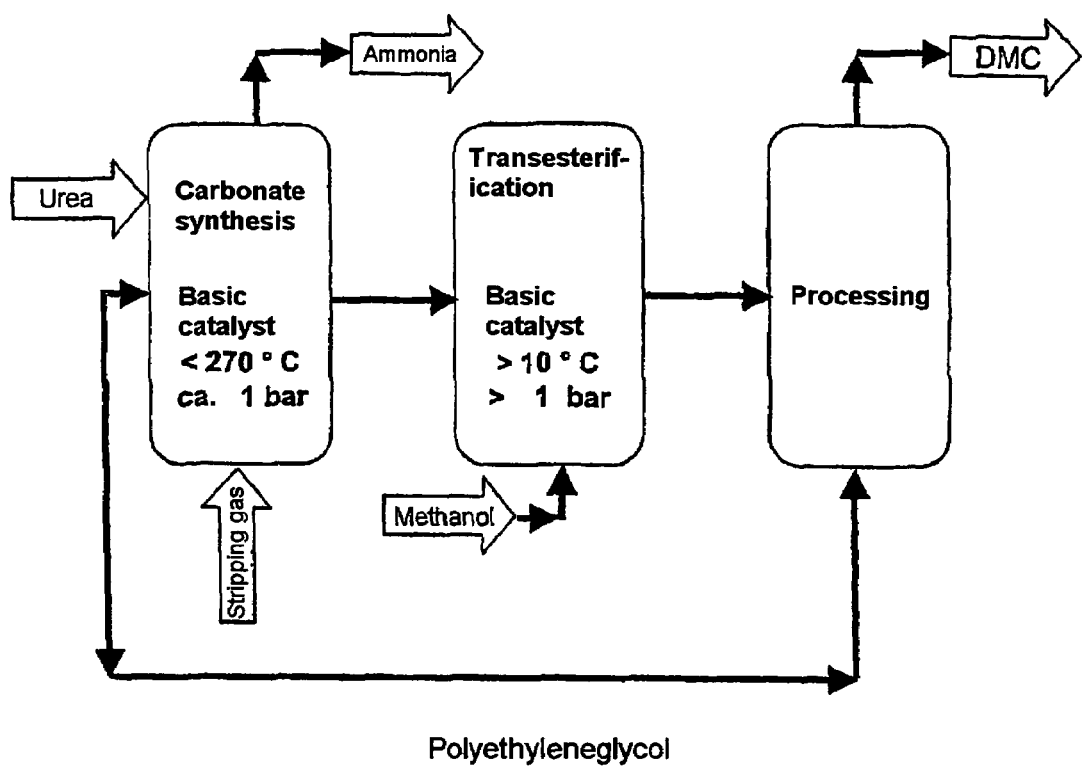
Fig. 1: Example of an engineering arrangement of method for manufacturing organic carbonates, for example DMC manufacture

METHOD FOR THE PRODUCTION OF ORGANIC CARBONATES

CROSS REFERENCE TO RELATED APPLICATIONS

This application is the US national phase of PCT application PCT/EP2004/007911 filed 16 Jul. 2004 with a claim to the priority of German patent application 10341953.5 itself filed 11 Sep. 2003.

The object of the invention is a two-stage method for the manufacture of organic carbonates.

Dimethyl carbonate and diphenyl carbonate are intermediates in the chemical industry, which are employed in a multiplicity of application areas. Thus dimethyl carbonate is a starting material for aromatic polycarbonates. Dimethyl carbonate is transesterified with phenol to diphenyl carbonate and converted in a melt polymerization with bisphenol to the aromatic polycarbonate (Daniele Delledonne; Franco Rivetti; Ugo Romano: "Developments in the Production and Application of Dimethyl Carbonate" Applied Catalysis A: General 221 (2001) 241-251). Dimethyl carbonate can be employed for improvement of the octane number of gasoline and substituted for environmentally troublesome additives like MTBE (Michael A. Pacheco; Christopher L. Marshall: "Review of Dimethyl Carbonate (DMC) Manufacture and its Characteristics as a Fuel Additive" Energy and Fuels 11 (1997) 2-29). In this connection, above all the easy biodegradability, the non-toxicity and the good applicability as a gasoline additive are to be mentioned. Dimethyl carbonate has a range of applications in chemical synthesis. At temperatures at or under the boiling point of 90° C. dimethyl carbonate can be used as a methoxylating agent. At higher temperatures around 160° C. dimethyl carbonate it can be employed as a methylating agent (Pietro Tundi; Maurizio Selva: "The Chemistry of Dimethyl Carbonate" Acc. Chem. Res. 35 (2002) 706-716).

Up until about 1980 the method used for the manufacture of dimthyl carbonate was the alcoholysis of phosgene with methanol (U.S. Pat. No. 2,379,740, Pittsburgh Plate Glass Company 1941) or (Kirk-Othmer, Encyclopedia of Chemical Technology, 3$^{rd}$ Edition, Volume 4, 758). The toxicity of phosgene and formation of corrosive hydrogen chloride of course stand against environmentally conscious commercial use on a large scale.

To date the process mainly utilized is the conversion of methanol with carbon monoxide and oxygen on a copper chloride contact, described in U.S. Pat. No. 5,210,269 from Enichem (1993). This oxidative carbonylation involves running over copper methoxy chloride and a subsequent reaction with carbon monoxide to dimethyl carbonate. The main problem of this process is the deactivation of the catalyst by water. The deactivated catalyst must be expensively regenerated or the water content in the reactor be held low.

A variant of the oxidative carbonylation is a two-stage reaction over methyl nitrite. Methyl nitrite is synthesized in a pre-reactor from methanol, nitric oxide and oxygen, wherein water arises as a byproduct. After removal of the water, gaseous methyl nitrite is converted to dimethyl carbonate in a solid bed reactor on a palladium chloride catalyst with CO; the NO produced is fed into this circuit. This method has the disadvantage that the operation with corrosive nitric oxide is dangerous.

Another possibility for the manufacture of dimethyl carbonate is the conversion of a cyclic carbonate with methanol. Methods with ethylene or propylene carbonate as starting material are known (U.S. Pat. No. 4,734,518 Texaco 1988; U.S. Pat. No. 4,691,041 Texaco 1987). Starting from the cyclic carbonate the dimethyl carbonate can be synthesized and simultaneously in each case one mole of the corresponding diol by transesterification with methanol. The alkylene carbonates can be simply prepared. The disadvantage of this method is the co-production of diols with the manufacture of dimethyl carbonate.

The direct alcoholysis of urea with methanol is another possibility for the manufacture of dimethyl carbonate. The synthesis goes in two steps via the carbamic acid methyl ester to the dimethyl carbonate. The reaction rate is strongly inhibited by the ammonia that is formed. For the improved synthesis therefore chemical and physical methods were proposed to remove the ammonia formed.

Also the precipitation of the ammonia formed by means of $BF_3$ was successfully performed (U.S. Pat. No. 2,834,799, 1958), but is however uneconomical in view of the higher salt loads arising.

The removal of ammonia (U.S. Pat. No. 4,436,668; BASF 1984) by addition of inert gas in a second stage provided up to now only unsatisfactory conversions and selectivities. For improvement of the process, a second stage was employed with a reacting catalyst diakyl isocyanate alkoxy tin (U.S. Pat. No. 5,565,603; Exxon 1996; U.S. Pat. No. 5,561,094; Exxon 1996), which is prepared in situ by methanol. As a disadvantage the preparation and processing of the reacting catalyst is to be mentioned.

An alternative to the direct synthesis is the utilization of a cyclic carbonate (U.S. Patent 5,489,702 Mitsubishi Gas Chemical 1996; U.S. Pat. No. 5,349,077; Mitsubishi Gas Chemical 1994). Here in a first step a diol is reacted with urea and a cyclic alkylene carbonate with 5 or 6 ring atoms is synthesized. In the second process step the alkylene carbonate is transesterified with methanol. The diol can subsequently be fed into the circuit.

The intermediate products prepared in the alcoholysis must subsequently be reacted with methanol, in order to obtain dimethyl carbonate as product. The transesterification is a catalyzed reaction. As heterogeneous catalysts basic alkali and alkaline earth metals or oxides are employed. Examples of alkali or alkaline earth metals in zeolites are in U.S. Pat. No. 6,365,787 from Exxon. Examples of metal oxides are mentioned in U.S. Pat. No. 6,207,850 Mobil Oil. Methods for the transesterification of ethylene and propylene carbonates with alcohols in counter current solid bed reactors with homogeneous or heterogeneous catalysts (U.S. Pat. No. 5,231,212; Bayer 1993; U.S. Pat. No. 5,359,188; Bayer 1994) as well as a method patent for the synthesis by means of epoxides with subsequent transesterification on bifunctional catalysts (U.S. Pat. No. 5,216,135; Bayer 1993) are likewise known already. The transesterification of cyclic carbonates with alcohols in a reactive distillation is described (U.S. Pat. No. 6,346,638; Asahi Kasai Kabushiki Kaisha 2002). A reactive extraction with hydrocarbons or gasoline as a phase for the absorption of dimethyl carbonate and a polar phase of alkylene carbonate for absorption of the alcohols is known from U.S. Pat. No. 5,489,703.

Only a few of these are in principle possible synthesis routes for a prospective engineering and economical realization. For the required large quantities of dimethyl carbonate only those methods come into consideration which also have available in sufficient quantities the necessary inexpensive raw materials. In recent years therefore the manufacture of organic carbonates preferably dimethyl carbonate, on the basis of urea and methanol, has been strenuously worked on to implement on an engineering scale. Despite numerous developments the methods described up to now in part possess significant disadvantages, so that an elegant engineering route for the production of organic carbonates, such as DMC is still lacking.

As disadvantageous the methods described up to now show:

The reaction of urea with methanol proceeds via the intermediate stage of carbamates.

During the reaction ammonia is split off, which must be removed.

The reaction because of insufficient ammonia proceeds with only small degrees of conversion.

Ammonia can in principle be removed from the reaction mixture via different methods, however in the methods known from the state of the art, in this connection a solid material to be disposed of forms or a major part of the methanol employed is also removed.

Large amounts of methanol must be utilized in the circuit.

A method developed for DMC can not without further ado be extended to the synthesis of other carbonates.

A method would be advantageous which permitted the synthesis of dimethyl carbonate and other organic carbonates, without the above disadvantages being present. At the same time it would be desirable if through a new method, the intermediate products necessary for the dimethyl carbonate synthesis had a higher boiling point, so that in the necessary removal of ammonia they are not removed together. It would be specially advantageous if a method were to be available, which did not require pure materials as aids for the manufacture of intermediate products, but could permit mixtures, in order on the one hand to achieve an improved urea solubility and on the other hand to positively influence the boiling behavior. Moreover it would be advantageous if the aids employed here were environmentally neutral.

These goals could be achieved with the new method for manufacture of organic carbonates presented here.

The object of the invention is therefore a method for manufacture of organic carbonates, in which urea, a substituted urea, a salt or ester of carbamic acid or one of its N-substituted derivatives (alkyl, aryl groups like methyl, ethyl, phenyl, benzyl)

In a first stage with polymeric multifunctional alcohols like polyalkyleneglycols, polyester polyols or polyether polyols of the general formula I H—[O—R]$_n$—OH     (formula I)

in which R stands for a straight chain or branched chain alkylene group having 2 to 12 carbon atoms and n is a number between 2 and 20, or completely or partially hydrolyzed polyvinylalcohols of the general formula II

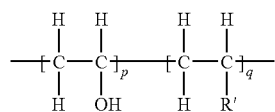

(formula II)

In which R' stands for an alkyl, aryl or acyl group having 1-12 carbon atoms, and p and q are numbers between 1 and 20 or dissolved in mixtures of these compounds, without or in the presence of catalyst favoring splitting off of ammonia is converted to a carbonate and carbamate containing mixture, which thereby removes free becoming ammonia or the amine from the reaction mixture by means of a stripping gas and/or steam and/or vacuum and In a second stage (transesterification) the carbonates and carbamates of the polymeric alcohols containing mixture is reacted with an alcohol or a phenol with formation of their carbonates and back formation of the polymeric polyalcohols of formulas I or II.

Up to now for the manufacture of the carbamate intermediate product according to the state of the art monomeric glycol and monomeric diols are utilized with urea (Michael A. Pacheco; Christopher L. Marshall: "Review of Dimethyl Carbonate (DMC) Manufacture and its Characteristics as a Fuel Additive" Energy & Fuels 11 (1997) 2-29). This is carried out in the first stage in order to produce the carbonates of these alcohols.

Surprisingly it has now been shown that the utilization of polymeric alcohols (polyols) has a series of essential advantages in contrast to the state of the art.

Polymeric alcohols and the carbonates and carbamates formed from them possess an essentially higher boiling point than the monoalcohols, diols and the carbonates and carbamates formed from them, described up until now in the state of the art. This results in that in the removal of the ammonia arising from the reaction by stripping or vacuum, an almost complete conversion and at the same time minimal loss of these higher boiling alcohols and carbonates or carbamates is achieved. This is not possible by use of the methods known from the state of the art, since upon stripping also large proportions of the alcohols used there and the glycol carbonates or diol carbonates are driven out of the reaction mixture.

Due to their water-like polar structure polymeric alcohols possess a higher solubility for urea, substituted ureas, salts and esters of carbamic acid and its N-substituted derivatives than the long chain monoalcohols or diols used up to now, so that the conversions can be carried out in homogeneous solution. Through changing the chain length n and the size of the subgroups R the solubility and at the same time the boiling point of the mixture desired can be set. Additionally polymeric alcohols are still liquid at temperatures at which comparably long monoalcohols or diols are already solid.

Furthermore these auxiliary materials have an adjustable viscosity are less corrosive and are consequently specially suited for a circuit way of operation. Further they are not toxic and consequently environmentally neutral.

Polymeric alcohols posses a distinctly higher chemical, thermal and mechanical stability than the materials used up to now, which for recovery (circuit operation) of these alcohols after the back formation in the second stage is a large advantage, since the loss of polymeric alcohols due to decomposition or thermal cracking processes are minimal.

Normally one would not think of employing polymeric alcohols for the purpose of intermediate formation because polymeric alcohols are multicomponent mixtures, which are more difficult to handle from an engineering standpoint than pure auxiliary materials. The multicomponent mixture produced when polymeric alcohols are employed is caused as a rule by the further processing difficulties. However directly through the employment of polymeric alcohols here an engineering advantage is produced. Because it has been surprisingly shown that it is not at all necessary to process the resulting multicomponent mixture, but that one can proceed directly to the second stage (transesterification) without disadvantages arising hereby. Because in the transesterification with lower alcohols or phenols, all initially present polymeric alcohols form back completely exactly as the usually used monoalcohols or diols. These can then be fed again to the first stage (circuit way of operating).

BRIEF DESCRIPTION OF THE DRAWING

An advantageous embodiment of a method for the manufacturing organic carbonates is presented in FIG. 1.

Important features of the method in accordance with the invention are:

Conversion of urea, substituted ureas, salts and esters of carbamic acid and its N-substituted derivatives with polymeric alcohols to high boiling carbonates in one stage.

High conversions and yields through simultaneous removal (stripping with gas and/or steam or vacuum installation) of the ammonia arising in the reaction with minimal losses of alcohols, carbonates and carbamates.

The reaction in the first stage does not require a catalyst, however through the employment of basic catalysts a further increase of the reaction rate can be achieved.

Production of the desired carbonates in a second stage through simple transesterification of the high boiling carbonates from a first stage.

The polymeric alcohols employed as auxiliary materials are fed into the circuit, without needing an expensive processing.

A variable method is involved that can also be employed for the manufacture of carbonates of straight chain or branched chain alcohols having 2-10 carbon atoms, not only for dimethyl carbonate.

The method can likewise be also used for the manufacture of carbonates of substituted phenols, which have alkyl groups with 1-4 carbon atoms, therefore not only for the manufacture of diphenyl carbonate, because the boiling points of the intermediate products are high and far removed from the boiling points of the alcohols or phenols employed in the transesterification. Thereby a better separation of the desired carbonate and the back-formed auxiliary materials is possible over a wider temperature range.

The effectiveness of the new method proposed here in accordance with the invention for the manufacture of organic carbonates should be made clear on the basis of a few examples.

The method in accordance with the invention is carried out in both stages in an advantageous way at temperatures between 10° C. and 270° C. In the first stage is processed under normal pressure and dosage of one of the suitable gases or steam for driving out the ammonia formed in the presence of catalysts. For this alkaline reacting salts, oxides, hydroxides, alcoholate of the first and second main group or of the 1 to 8 subgroupDONE of the periodic system, basic zeolites or polymeric ion exchangers are suitable. For example magnesium or zinc catalysts which can be employed as the oxide or also as well as by the acetate can be catalytically effective. An important influencing quantity is the removal of ammonia through stripping with gas, steam or vacuum.

The second stage contains the transesterification of carbonate or carbamate with an alcohol or a phenol and canb be carried out in the presence of the same basic catalysts as in the first stage. The use of quaternary ammonium salts such as tetrabutylammoniumacetate or tetrabutylammonium bromide or magnesium alcoholates have been shown as being specially advantageous. The transesterification is an equilibrium reaction whose position lies most likely on the side of output material, so that a simultaneous reaction and material separation is significant. Temperatures between 10° C. and 270° C. permit a relatively broad transesterification in this stage.

The invention is explained in detail by means of the following tests.

Test Construction and Implementation

All tests for the transesterification of the urea dissolved in a polymeric alcohol were carried out in a 150 ml double-mantle glass reactor with a heating mantle, gassing device and reflux condenser. A drop separator before the entry into the reflux condenser prevented the discharge of carried-over liquid. As stripping gas nitrogen was employed. Vacuum could be employed by means of an attached membrane pump. Samples were taken discontinuously.

Investigations with Polyethyleneglycol

Polyethyleneglycol is a suitable reactant, since it has a range of interesting properties. The transesterification of the bivalent alcohol with urea can in principle produce two products. These two long-chain carbonates are:

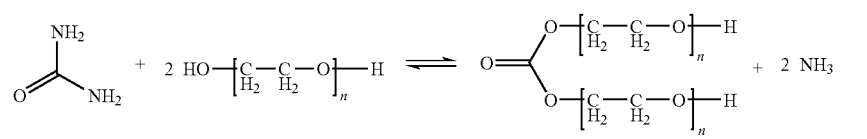

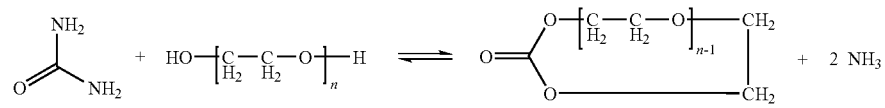

Both carbonates are suited for the transesterification to the desired product in the second stage with methanol. The investigations showed that the reaction to the cyclic carbonate is more likely, since the reaction takes place in a ratio of 1 mole urea to 1 mole polyethylene glycol. In both cases the carbamate is to be observed as intermediate product:

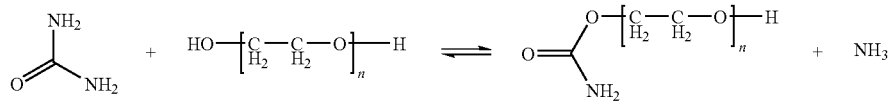

Use of Different Catalysts

The catalysts named in the patent literature comprise a series of metal oxides. In the tests carried out in accordance with the invention, oxide and acetate powders came to be employed. They were employed in mass ratios between 5 and 25 wt %. Titanium dioxide, zinc oxide, magnesium oxide and magnesium acetate were investigated as possible catalysts.

In that connection only small differences in the reaction outcome were evident for these different catalysts. The reaction rate was also very low at 150° C. and even after 16 hours completion of the transesterification was not visible.

The acceleration of the reaction was with magnesium acetate, magnesium oxide and zinc oxide. These compounds showed a clearly improved catalytic activity compared with titanium compounds.

An increase of the amount of catalyst was investigated, but did not bring the hoped for difference in the reaction rate. At 150° C. there was as good as no difference could be seen between the tests with 6 or 20 g magnesium acetate. Also at higher temperature of 200° C. after an initially faster development of product, no clear difference in amount of product obtained was to be discerned.

Variation of the Temperature

Previous tests of reactions of urea with polyethyleneglycol have shown that below about 140° C. as good as no reaction is to be observed. Therefore 150° C. was chosen as minimal test temperature. In the tests with titanium dioxide a moderate volume stream of nitrogen was used to drive off the ammonia. A clear influence of the reaction temperature in raising the level from 150 to 200° C. in the course of the polyethyleneglycol concentration was not discernible. It showed that at 200° C. a nearly complete conversion was achieved after 5 hours, while at 150° C. very little product develops.

Use of Vacuum or Stripping Gas (Nitrogen)

Driving off the ammonia formed from the reaction mixture by means of vacuum or stripping with nitrogen was identified as the main parameter influencing the reaction of urea with polyethyleneglycol. Operation under vacuum was investigated in two tests at a pressure of 300 mbar. A marked improvement of the conversion behavior in comparison to the reaction without driving off the ammonia formed at ambient pressure was evident. Still better results were obtained in the gas treatment of the reaction mixture with nitrogen. A variation of the stream volume showed a distinct influence on the reaction of urea with polythyleneglycol.

The subsequent transesterification of the polymeric carbonates and carbamates was carried out with methanol or phenol in the presence of tetraalkylammonium salts or magnesium methylate, wherein after processing the reaction products the desired carbonates are obtained.

By means of the method in accordance with the invention the production of organic carbonates is possible via the intermediate stage of a mixture of organic carbonates and carbamates with polymeric groups by means of the reaction of urea or urea derivatives with polymeric alcohols like polyethyleneglycol, at normal pressure, temperatures of up to 270° C. and addition of up to 5 wt % of alkaline reacting catalysts. The products obtained in the first stage are exclusively organic carbonates and carbamates of the corresponding polymeric alcohols. For reaction times of about 5 hours conversions of over 90% were achieved.

An important influencing value for the obtaining of higher conversions is the stream volume of stripping gas. At sufficiently stream volumes the removal of ammonia is no longer the rate-determining step.

The conversion of the carbonates or carbamates with methanol produced in the first stage proceeds relatively quickly with a basic catalyst, with use of a slightly increased pressure of ca. 6 bar at a temperature of ca. 140° C. The equilibrium is established after less than 1 hour in batch operation. As catalyst a quaternary ammonium salt was employed, which showed good catalytic properties. Still higher reaction rates were achieved through use of magnesium methylate.

In the coupling in accordance with the invention of both stages the polymeric alcohol used as auxiliary alcohol is fed back again into the first stage after separation of the dimethyl carbonate. By means of operating the method in a loop the losses of the polymeric auxiliary alcohol are avoided, so that the method is to be seen as exceedingly economical.

The invention claimed is:

1. A method for the manufacture of organic carbonates, comprising converting urea, a substituted urea, a salt or ester of carbamic acid or one of its N-substituted derivatives in a first stage with a polymeric alcohol of the general formula I

in which R stands for a straight chain or branched chain alkylene group having 2 to 12 carbon atoms and n is a number between 2 and 20, or with a complete or partially hydrolyzed polyvinylalcohol of the general formula II

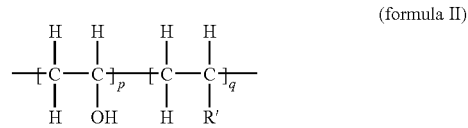

in which R' stands for an alkyl, aryl or acyl group having 1-12 carbon atoms, p and q are numbers between 1 and 20, or dissolved in mixtures of these compounds, without or in the presence of an ammonia splitting catalyst, which converting is to a carbonate and carbamate containing mixture, and a thereby liberated ammonia or amine is removed by means of a stripping gas and/or steam and/or vacuum, and in a second stage a mixture containing the carbonate and carbamate is reacted with an alcohol or a phenol with formation of their carbonates and back formation of the polymeric alcohol or polyvinylalcohol of formulas I or II.

2. The method according to claim 1, wherein the polymeric alcohol of polyvinylalcohol of formulas I or II back-formed in the second stage are completely or partially fed back again to the first stage.

3. The method according to claim 1, wherein both the first stage and the second stage are carried out at temperatures between 10° and 270° C.

4. The method according to claim 1, wherein both the first stage and the second stage are conducted in the presence of a catalyst of alkaline reacting salts, oxides, hydroxides, alcoholates with elements of groups Ia, Ib, IIa, IIb, IIIa, IIIb, IVa, IVb, Va, Vb, VIIb, VIIIb of the periodic system, basic zeolites, polymeric ion exchangers or tetraalkylammonium salts or triphenylphosphine or tertiary amines.

5. The method for the manufacture of organic carbonates according to claim 1, wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

6. The method according to claim 2 wherein both the first stage and the second stage are carried out at temperatures between 10° and 270° C.

7. The method according to claim 2 wherein both the first stage and the second stage are conducted in the presence of a catalyst of alkaline reacting salts, oxides, hydroxides, alcoholates with elements of groups Ia, Ib, IIa, IIIb, IIIa, IIIb, IVa, IVb, Va, Vb, VIIb, VIIIb of the periodic system, basic zeolites, polymeric ion exchangers or tetraalkylammonium salts or triphenylphosphine or tertiary amines.

8. The method according to claim 3 wherein both the first stage and the second stage are conducted in the presence of a catalyst of alkaline reacting salts, oxides, hydroxides, alcoholates with elements of groups Ia, Ib, IIa, IIIb, IIIa, IIIb, IVa, IVb, Va, Vb, VIIb, VIIIb of the periodic system, basic zeolites, polymeric ion exchangers or tetraalkylammonium salts or triphenylphosphine or tertiary amines.

9. The method according to claim 6 wherein both the first stage and the second stage are conducted in the presence of a catalyst of alkaline reacting salts, oxides, hydroxides, alcoholates with elements of groups Ia, Ib, IIa, IIIb, IIIa, IIIb, IVa, IVb, Va, Vb, VIIb, VIIIb of the periodic system, basic zeolites, polymeric ion exchangers or tetraalkylammonium salts or triphenylphosphine or tertiary amines.

10. The method for the manufacture of organic carbonates according to claim 2 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

11. The method for the manufacture of organic carbonates according to claim 3 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

12. The method for the manufacture of organic carbonates according to claim 4 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

13. The method for the manufacture of organic carbonates according to claim 6 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

14. The method for the manufacture of organic carbonates according to claim 7 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

15. The method for manufacturing organic carbonates according to claim 8 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

16. The method for manufacturing organic carbonates according to claim 9 wherein the second stage is conducted with methylalcohol and/or straight chain or branched aliphatic alcohols having 2 to 10 carbon atoms and/or cyclic alcohols having 5 to 10 carbon atoms or phenol and/or substituted phenols, which have alkyl groups with 1 to 4 carbon atoms and/or aromatic alcohols which have 6 to 20 carbon atoms and/or alcohols containing heteroatoms and/or a mixture of these materials.

* * * * *